United States Patent
Hara et al.

(10) Patent No.: US 10,586,091 B2
(45) Date of Patent: Mar. 10, 2020

(54) TENPRINT CARD INPUT DEVICE, TENPRINT CARD INPUT METHOD AND STORAGE MEDIUM

(71) Applicant: NEC Corporation, Tokyo (JP)

(72) Inventors: Masanori Hara, Tokyo (JP); Tatsuya Shimahara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 15/042,289

(22) Filed: Feb. 12, 2016

(65) Prior Publication Data

US 2016/0162723 A1   Jun. 9, 2016

Related U.S. Application Data

(63) Continuation of application No. 14/112,922, filed as application No. PCT/JP2012/060359 on Apr. 17, 2012, now Pat. No. 9,361,506.

(30) Foreign Application Priority Data

Apr. 20, 2011   (JP) ................................. 2011-094029

(51) Int. Cl.
| | | |
|---|---|---|
| G06K 9/00 | (2006.01) | |
| G06K 9/34 | (2006.01) | |
| G06T 7/73 | (2017.01) | |
| A61B 5/1172 | (2016.01) | |

(52) U.S. Cl.
CPC ....... G06K 9/00067 (2013.01); G06K 9/0008 (2013.01); G06K 9/00013 (2013.01); G06K 9/346 (2013.01); G06T 7/74 (2017.01); A61B 5/1172 (2013.01); *G06T 2207/10004* (2013.01)

(58) Field of Classification Search
None
See application file for complete search history.

(56) References Cited

U.S. PATENT DOCUMENTS

| 5,650,842 A | 7/1997 | Maase et al. |
| 6,047,079 A | 4/2000 | Uchida |
| (Continued) | | |

FOREIGN PATENT DOCUMENTS

| EP | 0653724 A2 | 5/1995 |
| EP | 0 653 724 B1 | 2/2000 |
| (Continued) | | |

OTHER PUBLICATIONS

Slap fingerprint segmentation evaluation 2004, Nov. 6, 2010, pp. 1-3.*

(Continued)

*Primary Examiner* — Jayesh A Patel
(74) *Attorney, Agent, or Firm* — McGinn I. P. Law Group, PLLC

(57) ABSTRACT

A fingerprint image processing device includes a memory, and a processor coupled to the memory. The processor performs operations, including reading a tenprint card image which includes a plurality of fingerprint patterns and at least one ruled line to separate one fingerprint imprint area from another fingerprint imprint area, and extracting from the tenprint card image a fingerprint image which includes a part of a fingerprint imprint area and apart of a next fingerprint imprint area.

19 Claims, 20 Drawing Sheets

(56) References Cited

U.S. PATENT DOCUMENTS

| | | | |
|---|---|---|---|
| 6,151,426 A * | 11/2000 | Lee | H04N 1/3872 382/319 |
| 6,282,302 B1 * | 8/2001 | Hara | G06K 9/00013 382/116 |
| 7,072,496 B2 * | 7/2006 | Lo | G06K 9/00013 340/5.53 |
| 7,203,344 B2 | 4/2007 | McClurg et al. | |
| 7,308,122 B2 | 12/2007 | McClurg et al. | |
| 7,941,541 B2 * | 5/2011 | Chang | H04L 12/2805 709/227 |
| 9,361,506 B2 * | 6/2016 | Hara | G06K 9/0008 |
| 9,965,233 B2 * | 5/2018 | Chang | G06Q 20/327 |
| 2003/0123716 A1 | 7/2003 | Scott | |
| 2003/0128240 A1 | 7/2003 | Martinez et al. | |
| 2003/0133143 A1 | 7/2003 | McClurg et al. | |
| 2003/0142856 A1 | 7/2003 | McClurg et al. | |
| 2004/0120555 A1 * | 6/2004 | Lo | G06K 9/00013 382/124 |
| 2005/0036708 A1 * | 2/2005 | Boll | H04N 1/00241 382/283 |
| 2005/0180619 A1 | 8/2005 | McClurg et al. | |
| 2006/0002595 A1 | 1/2006 | Hara et al. | |
| 2006/0026507 A1 | 2/2006 | Balinsky et al. | |
| 2007/0041622 A1 | 2/2007 | Salva Calcagno | |
| 2008/0298648 A1 | 12/2008 | Lo et al. | |
| 2011/0310414 A1 * | 12/2011 | Morimoto | G03G 15/5025 358/1.9 |

FOREIGN PATENT DOCUMENTS

| | | | | |
|---|---|---|---|---|
| JP | 7-168925 A | | 7/1995 | |
| JP | 2003-173445 A | | 6/2003 | |
| JP | 2003-346155 A | | 12/2003 | |
| JP | 2004-078434 A | | 3/2004 | |
| JP | 2005-516290 A | | 6/2005 | |
| JP | 2006-018731 A | | 1/2006 | |
| JP | 2006-146741 A | | 6/2006 | |
| JP | 2008-040693 A | | 2/2008 | |
| JP | 2008040693 A | * | 2/2008 | ............ G06K 9/0008 |
| JP | 2008040693 A | * | 2/2008 | ............ G06K 9/0008 |
| JP | 6323437 B2 | | 5/2018 | |

OTHER PUBLICATIONS

Roll versus Plain . . . Database, Nadgir et al. Jun. 2006. pp. 1-11.*
Example of a Tenprint card image, p. 1.*
Roll versus Plain . . . Database, Nadgir et al. Jun. 2006. pp. 1-11 (Year: 2006).*
Slap fingerprint segmentation for live-scan devices and ten-print cards, Yong-Liang Zhang et al., IEEE, 1051-4651, 2010, pp. 1180-1183 (Year: 2010).*
State of the Art Biometrics Excellence Roadmap, Destini Davis et al., Mitre Technical Report, Oct. 2008, pp. 1-1 to 6-2 (Year: 2008).*
Latent Fingerprint Matching: Fusion of Rolled and Plain Fingerprints, Feng et al., Springer, 2009, pp. 695-704 (Year: 2009).*
United States Notice of Allowance dated Feb. 18, 2016 in U.S. Appl. No. 14/112,922.
U.S. Office Action dated Apr. 3, 2015 in co-pending U.S. Appl. No. 14/112,922.
U.S. Office Action dated Aug. 13, 2015 in co-pending U.S. Appl. No. 14/112,922.
English Translation of PCT/ISA/237 (written opinion of the international searching authority, dated May 22, 2012).
European Patent Office Search Report dated Dec. 8, 2014.
Ulery, et al., NISTIR 7209 "Slap Fingerprint Segmentation Evaluation 2004 SlapSeg04 Analysis Report", Mitretek Systems, NIST, Mar. 8, 2005, XP55125924, pp. 1-60.
PCT/IB/373 dated Oct. 22, 2013.
Roll versus Plain Prints—Database, Nadgir et al., West Virginia University, Morgantown, WV 26506, Jun. 2006, pp. 1-11.
Dempster-Shafer—performance, Singh et al, ICVGIp 2006, LNCS 4338, 2006, pp. 941-949.
Quality augmented fusion—theory, Vatsa et al, Elsevier, 2008 pp. 1-11.
International Search Report in PCT/JP2012/060359 dated May 22, 2012 (English Translation Thereof).
"The Science of Fingerprints" by John Edgar Hoover, US DOJ,FBI; 1984, [online],[Searched on Apr. 5, 2011], Internet, (URL:http://www.gutenberg.org/files/19022/19022-h/19022-h.htm).
"ANSI/NIST-ITL-1-2000 Data Format for the Interchange of Fingerprint, Facial, & Scar Mark & Tattoo (SMT) Information", [online],[Searched on Apr. 5, 2011], Internet, (URL:ftp://sequoyah.nist.gov/pub/nist_internal_reports/sp500-245-a16.pdf).
"NISTIR 7209 Slap Fingerprint Segmentation Evaluation 2004(SlapSeg04 Analysis Report)",[online], [Searched on Apr. 5, 2011], Internet(URL:http://www.nist.gov/itl/iad/ig/upload/ir_7209.pdf).
Office Action, dated Oct. 31, 2016, of corresponding JP Application No. 2015-239243 and English translation of relevant portions thereof.
Office Action (dated Aug. 16, 2017) of corresponding JP Application No. 2015-239243, and English translation thereof.
Extended European search report, dated Sep. 19, 2018 in European Application No. 18181600.0.
Decision to Grant a Patent, dated May 28, 2019, in Japanese Application No. 2018-076672 and English Translation thereof.

* cited by examiner

TENPRINT CARD INPUT DEVICE, TENPRINT CARD INPUT METHOD AND STORAGE MEDIUM

The present application is a Continuation application of U.S. patent application Ser. No. 14/112,922, filed on Oct. 19, 2013, which is based on International Application No. PCT/JP2012/060359, filed on Apr. 17, 2012, which is based on Japanese Patent Application No. 2011-094029, filed on Apr. 20, 2011, the entire contents of which are incorporated herein by reference.

TECHNICAL FIELD

The present invention relates to a tenprint card input device which creates a digital image of a tenprint card for inputting.

BACKGROUND ART

Generally, since a fingerprint composed of many ridges with striped pattern has two important characteristics of "permanence" and "uniqueness", it has been used for a person authentication method for a long time. Particularly, matching by using fingerprints left on the crime scene is an effective investigation method.

Recently, in many police agencies, a fingerprint matching system using a computer (a computing machine) has been introduced, and left fingerprint matching has been performed. As objects of the left fingerprint matching, a database of tenprint cards taken from criminals (suspects and arrestees) has been made.

Ten fingers are 10 fingers of both hands. The 5 fingers of the single hand are called a thumb finger, an index finger, a middle finger, a ring finger and a little finger.

As described in a non-patent literature 1 of "The Science of Fingerprints", the tenprint card includes a total of fourteen kinds of images (14 images) containing ten kinds of rolled prints and four kinds of plane prints or slap prints.

Here, it is assumed that, in the tenprint card, ten kinds of rolled print image frames (ruled line frame) and four kinds of slap print image frames (ruled line frame) are already printed.

The rolled print images are fingerprints of a thumb finger, an index finger, a middle finger, a ring finger and a little finger of both hands individually imprinted while these fingers are rolled from side to side, and are images widely taken containing right and left side portion regions of the fingers by rolling the fingers. That is, the rolled print images include a total of ten images (ten kinds of rolled print images) that are two images of rolled prints of a thumb finger, an index finger, a middle finger, a ring finger and a little finger of both hands.

The slap print images are images taken containing fingertip region of the fingers by not rolling the fingers from side to side but standing the fingers at front. The slap prints include: a thumb-finger slap (a slap print of a thumb finger) that a fingerprint of the thumb finger is individually imprinted; and a four-finger slap (four kinds of slap prints) that fingerprints of the other four fingers (an index finger, a middle finger, a ring finger and a little finger) are simultaneously imprinted. That is, the slap print images includes a total of four images that are two images of the thumb-finger slaps of the right and left hands and two images of the four-finger slaps of the right and left hands.

Accordingly, the tenprint card has the fourteen kinds of images and the rolled prints of ten fingers and the slap prints of ten fingers are printed in it.

In a non-patent literature 2 of "ANSI/NIST-ITL-1-2000 Data Format for the Interchange of Fingerprint, Facial, & Scar Mark & Tattoo (SMT) Information" standardized in U.S. NIST (National Institute of Standards and Technology), a rule for creating a digital image by scanning a fingerprint image on the tenprint card is regulated.

This rule defines that fourteen individual images are created as digital images by segmenting the images along image frames on the tenprint card.

Furthermore, in this explanation, fingerprint images created as digital images with resolution of "500 ppi" are used based on this rule.

The slap print images are also used for checking a finger position error (an error of imprinting position) of the rolled prints by comparing the slap print images with the rolled print images.

The error of imprinting position is also called an error of imprinting sequence and this check is called a sequence check. The sequence check executed by a computer has started from the 1990's. This starts with segmenting individual fingers from the four-finger slap image. Segmenting the individual fingers from the four-finger slap is called slap fingerprint segmentation or slap segmentation.

A non-patent literature 3 of "NISTIR 7209 Slap Fingerprint Segmentation Evaluation 2004 (SlapSeg04 Analysis Report)" issued by U.S. NIST describes accuracy and problems regarding the slap fingerprint segmentation.

Recent fingerprint matching system is aimed at improving a hit rate of a left fingerprint by registering not only ten fingers of the rolled print images on the tenprint card but also ten fingers of the slap print images in the database and using them as objects for left fingerprint matching.

As described in the non-patent literature 1, appropriate fingerprint detection is that fingerprints are imprinted completely inside the image frames (the ruled line frames) printed on the tenprint card. However, since a criminal who is fingerprinted may be uncooperative for taking fingerprints, the taken fingerprint images may be protruded from the frames without appropriately imprinted inside the frames.

As a related art, a patent literature 1 (Japanese patent publication JP-Heisei 07-168925A) discloses a tenprint card input device. The tenprint card input device includes: a tenprint card image input section inputting image data of a tenprint card by an image scanner and so on; a data process section; an image storage section; a display device; a pointing device; and a segmented fingerprint image output section outputting fingerprint image data segmented in units of fingers. A segmentation information input section of the data process section memorizes the input tenprint card image data into the image storage section, overlaps ten segmentation frames for specifying respective segmentation ranges with the tenprint card image to displays them on the display device, and makes an operator input segmentation information for each finger. A segmentation editor section segments fingerprint images of respective fingers from the tenprint card image data of the image storage section based on the segmentation information, and edits and outputs the segmented fingerprint image.

In addition, a patent literature 2 (Japanese patent publication JP2003-173445A) discloses a fingerprint matching method and device. This related technique extracts the area of a region as core line stability, the region containing no feature point which is composed of points that a ridge of a fingerprint pattern diverges and points that a ridge ends and the region including a predetermined attention point as a center of the region, and then uses the region for matching.

Furthermore, a patent literature 3 (Japanese patent publication JP2004-078434A) discloses a striped pattern image appraising device and a striped pattern image. In this related technique, a feature point data matching section creates information of pair feature points. A core line data matching section creates information of core line points of a search side and a file side which make a pair. An image deformation correction section corrects data of the file side and reduces deformation of an image by using not only the information of the pair feature points but also the information of the core line points making a pair. An appraisive image edition display section outputs both of data of the search side and the corrected data of the file side in order to easily appraise the data. For example, the section overlaps the data of the search side with the corrected data of the file side and outputs them.

Moreover, a patent literature 4 (Japanese patent publication JP 2008-040693A) discloses a line noise removing device, a line noise removing method and a line noise removing program. This line noise removing device includes an image binarization section, a line noise certainty factor calculation section, a line noise region determination section, a density conversion section and an image synthesis section. The image binarization section creates a binary image by binarizing an input image. The line noise certainty factor calculation section creates a rotation image which the binary image is rotated for each of a plurality of rotation angles, calculates an edge feature value for each region continuing black pixels of each rotation image, and calculates a line noise certainty factor. The line noise region determination section selects a rotation angle candidate from the rotation angles, and determines a line noise region based on the line noise certainty factor, for the rotation image corresponding to each rotation angle candidate. The density conversion section creates a density conversion image by executes a local image enhancement on the region corresponding to the line noise region of the input image. The image synthesis section creates a synthesis image by synthesizing the density conversion images when a plurality of the rotation candidates is present.

CITATION LIST

Patent Literature

[PTL 1] JP-Heisei 07-168925A
[PTL 2] JP 2003-173445A
[PTL 3] JP 2004-078434A
[PTL 4] JP 2008-040693A Non Patent Literature

[NPL 1] "The Science of Fingerprints" by John Edgar Hoover, US DOJ, FBI; 1984, [online], [Searched on Apr. 5, 2011], Internet, (URL: http://www.gutenberg.org/files/19022/19022-h/19022-h.htm)
[NPL 2] "ANSI/NIST-ITL-1-2000 Data Format for the Interchange of Fingerprint, Facial, & Scar Mark & Tattoo (SMT) Information", [online], [Searched on Apr. 5, 2011], Internet, (URL: ftp://sequoyah.nist.gov/pub/nistinternal-reports/sp500-245-a16.pdf)
[NPL 3] "NISTIR 7209 Slap Fingerprint Segmentation Evaluation 2004 (SlapSeg04 Analysis Report)", [online], [Searched on Apr. 5, 2011], Internet (URL: http://www.nist.gov/itl/iad/ig/upload/ir_7209.pdf)

SUMMARY OF INVENTION

An object of the present invention is to provide a tenprint card input device which automatically segments individual fingerprint images on the tenprint card.

A tenprint card input device according to the present invention, includes: an image inputting device configured to create a digital image of a tenprint card and input it, the tenprint card being that ruled line frames for imprinting fingerprints of rolled prints and slap prints are preliminarily printed and rolled prints and slap prints are imprinted; a data processing device configured to automatically segment regions of rolled print images in ruled line frames and regions of slap print images including regions outside the ruled line frames from an image of the tenprint card, match the rolled print images against the slap print images, and segment fingerprint images for outputting by using the matching result; and an image outputting device configured to output the fingerprint images for outputting together with finger positions of the fingerprint images for outputting.

A tenprint card input method according to the present invention is a tenprint card input method executed by a computing machine and includes: creating a digital image of a tenprint card and inputting it, the tenprint card being that ruled line frames for imprinting fingerprints of rolled prints and slap prints are preliminarily printed and rolled prints and slap prints are imprinted; automatically segmenting regions of rolled print images in ruled line frames and regions of slap print images including regions outside the ruled line frames from an image of the tenprint card, matching the rolled print images against the slap print images, and segmenting fingerprint images for outputting by using the matching result; and outputting the fingerprint images for outputting together with finger positions of the fingerprint images for outputting.

A storage medium according to the present invention is a storage medium including a program that, when executed, causes a computing machine to perform the following: creating a digital image of a tenprint card and inputting it, the tenprint card being that ruled line frames for imprinting fingerprints of rolled prints and slap prints are preliminarily printed and rolled prints and slap prints are imprinted; automatically segmenting regions of rolled print images in ruled line frames and regions of slap print images including regions outside the ruled line frames from an image of the tenprint card, matching the rolled print images against the slap print images, and segmenting fingerprint images for outputting by using the matching result; and outputting the fingerprint images for outputting together with finger positions of the fingerprint images for outputting.

Consequently, appropriate fingerprint regions can be segmented from a tenprint card, and an error of imprinting position and an error of finger position specification can be reduced. Therefore, fingerprint matching accuracy can be improved.

DESCRIPTION OF EXEMPLARY EMBODIMENTS

Exemplary Embodiments

Exemplary embodiments of the present invention will be described below referring to the accompanying drawings.

[Tenprint Card Input Device]

Figure 1:
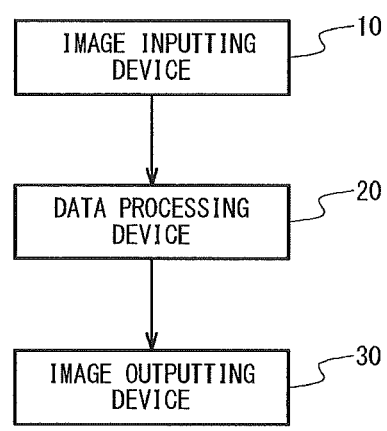
FIG. 1 is a view showing a configuration example of a tenprint card input device according to the present invention.

A configuration example of the tenprint card input device according to the present invention will be described with reference to FIG. 1.

The tenprint card input device according to the present invention includes an image inputting device 10, a data processing device 20 and an image outputting device 30.

The image inputting device 10 creates a digital image of the tenprint card taken by a camera, a scanner and so on and inputs it. In addition, the image inputting device 10 can input the tenprint card which has been created as a digital image and received from an external storage device and so on through a network.

The data processing device 20 segments individual fingerprint images from the tenprint card and creates individual fingerprint images. The data processing device 20 is realized by a processor which is driven and executes a predetermined processing based on a program, a memory which stores the program and various kinds of data and an interface (I/F) to the outside.

The image outputting device 30 outputs the segmented individual fingerprint images (the individual fingerprint images) and information of finger positions of the respective fingerprint images. The finger position indicates a kind of fingers such as a thumb finger, an index finger, a middle finger, a ring finger and a little finger.

[Data Processing Device]

Figure 2:
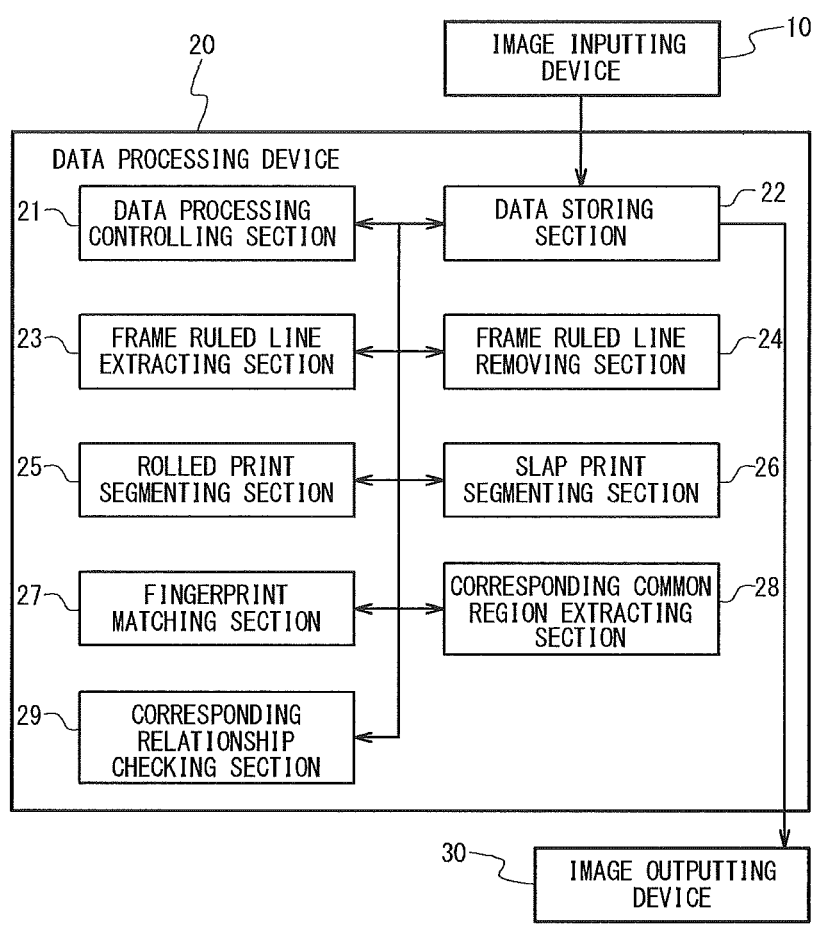
FIG. 2 is a view showing a configuration example of a data processing device.

A detail of the data processing device 20 will be described with reference to FIG. 2.

The data processing device 20 includes the data processing controlling section 21, the data storing section 22, the frame ruled line extracting section 23, the frame ruled line removing section 24, the rolled print segmenting section 25, the slap print segmenting section 26, the fingerprint matching section 27, the corresponding common region extracting section 28 and the corresponding relationship checking section 29.

The data processing controlling section 21 executes program control of all configuration elements of the data processing device 20 and controls the interface to the outside. Here, the data processing controlling section 21 controls internal configurations of the data processing device 20, the interface to the image inputting device 10 and the interface to the image outputting section 13.

The data storing section 22 provides work areas to respective elements of the data processing device 20 and temporarily stores data created by the respective elements of the data processing device 20.

The frame ruled line extracting section 23 analyzes the inputted image of the tenprint card and extracts ruled line frames for fourteen images. Here, the fourteen images are just one example.

The frame ruled line removing section 24 removes the ruled line frames for the fourteen images.

The rolled print segmenting section 25 segments rolled print images of ten fingers. Here, the ten fingers are just one example.

The slap print segmenting section 26 segments slap print images of four fingers for matching objects. Here, the four fingers are just one example.

The fingerprint matching section 27 individually matches the segmented rolled print images of ten fingers for searching against the slap print images for matching objects containing respective fingers. When finding regions similar to each other, the fingerprint matching section 27 outputs corresponding point information together with a matching score.

The corresponding common region extracting section 28 extracts a corresponding common region by using the corresponding point information as the matching result.

The corresponding relationship checking section 29 checks a corresponding relationship between the rolled prints and the slap prints and detects an error of imprinting position. In addition, the corresponding relationship checking section 29 assesses the finger positions and detects an error of imprinting finger position. If the corresponding relationship has inconsistency, there is possibility that the fingerprint imprinting position is wrong, and thus the corresponding relationship checking section 29 outputs a warning message indicating that fact.

[Example of Hardware]

Example of concretely hardware for realizing the tenprint card input device according to the present invention will be described below.

As an example of the image inputting device 10, a device which converts video pictures into electric signals by using a semiconductor element reacting to light like a CCD (Charge Coupled Device) and a CMOS (Complementary Metal Oxide Semiconductor) such as a scanner, a digital camera or a video camera is supposed. In addition, a cellular phone, a smart phone, a smart book, a car navigation system, a door phone, an intercom, a mobile game machine, a home video game machine, a mobile music player, a handy terminal, a gadget (an electric device), an interactive television, a digital tuner, a digital recorder, an information home appliance, an OA (an office automation) device, an ATM (automated teller machine), a point-of-sales terminal, a highly-functional copy machine, or a digital signage, which has a camera function, is also supposed. Furthermore, the image inputting device 10 may be a device for reading various information transmitting medium and an interface for obtaining information from an external input device and storage device.

As an example of the data processing device 20, a computing machine such as a PC (a personal computer), an appliance, a thin client server, a workstation, a main frame or a supercomputer is supposed. Here, the data processing device 20 may be an extension board mounted on a computing machine or may be a virtual machine (a VM) established on a physical machine.

As an example of the image outputting device 30, a display device such as a LCD (a liquid crystal display), a PDP (a plasma display panel) or an organic EL display (an organic electroluminescence display), a printing device which prints output contents on papers such as a printer or a projecting device which projects output contents on a wall or a screen such as a projector is supposed. In addition, the image outputting device 30 may be the same device as the image input device 10. Furthermore, the image output device 30 may be the interface for outputting information to external display devices, storage devices and so on.

The data processing device 20 may be connected to the image inputting device 10 and the image outputting device 30 through a network. As an example of the network, the Internet, a LAN (a local area network), a wireless LAN (a wireless local area network), a WAN (a wide area network), a backbone, a cable television (a CATV) line, a fixed-line phone network, a cellular phone network, the WiMAX (the IEEE 802.16a), the 3G (the 3rd generation), a lease line, an IrDA (an infrared data association, the Bluetooth (the registered trademark), a serial communication line or a data bus is considered.

Incidentally, the image inputting device 10, the data processing device 20 and the image outputting device 30 may be mounted on a mobile object such as a vehicle, a ship or an aircraft. The image inputting device 10, the data processing device 20 and the image outputting device 30 may be integrated.

As an example of the data processing controlling section 21, a processor is supposed. As an example of the processor, a CPU (a central processing unit), a NP (a network processor), a microprocessor, a microcontroller or a semiconductor integrated circuit (a LSI: large scale integration) having a dedicated function is considered.

As an example of the data storing section 22, a memory is supposed. As an example of the memory, a semiconductor memory device such as a RAM (a random access memory), a ROM (a read only memory), an EEPROM (an electrically erasable and programmable read only memory) or a flash memory, an auxiliary storage device such as a HDD (a hard disk drive) or a SSD (a solid state drive), or a storage medium such as a removable disk like a DVD (a digital versatile disk) or a SD memory card (a secure digital memory card) is considered. A buffer or a register may also be used. Or, a storage device such as a DAS (a direct attached storage), a FC-SAN (a fibre channel-storage area network), a NAS (a network attached storage) or an IP-SAN (an IP-storage area network) may be used.

Incidentally, the above processor and the above memory may be integrated. For example, recently, a microcomputer has been developing to be one chip. Accordingly, the case may be considered that one chip microcomputer mounted on an electric device includes both of the above processor and the above memory.

As examples of the frame ruled line extracting section 23, the frame ruled line removing section 24, the rolled print segmenting section 25, the slap print segmenting section 26, the fingerprint matching section 27, the corresponding common region extracting section 28 and the corresponding relationship checking section 29, the above processor or the combination of the above processor and the above memory is supposed. Here, each of the frame ruled line extracting section 23, the frame ruled line removing section 24, the rolled print segmenting section 25, the slap print segmenting section 26, the fingerprint matching section 27, the corresponding common region extracting section 28 and the corresponding relationship checking section 29 may be a module, a component or a dedicated device, or a boot (a calling) program thereof.

However, practically, they are not limited to these examples.

[Fingerprint Image Synthesis Processing]

Figure 3:
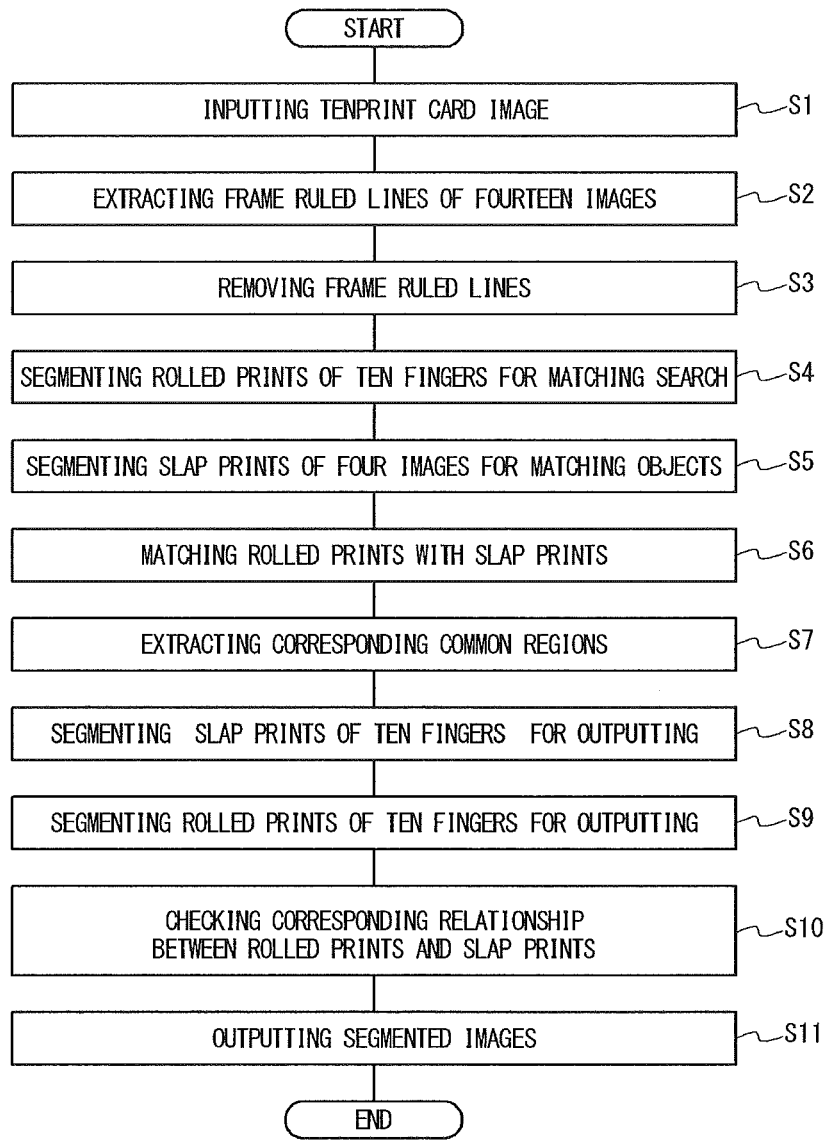
FIG. 3 is a flowchart showing an operation of a fingerprint image synthesis processing according to the present invention.

An operation flow of fingerprint image synthesis processing according to the present invention will be described with reference to FIG. 3.

(1) Step S1

Figure 4:
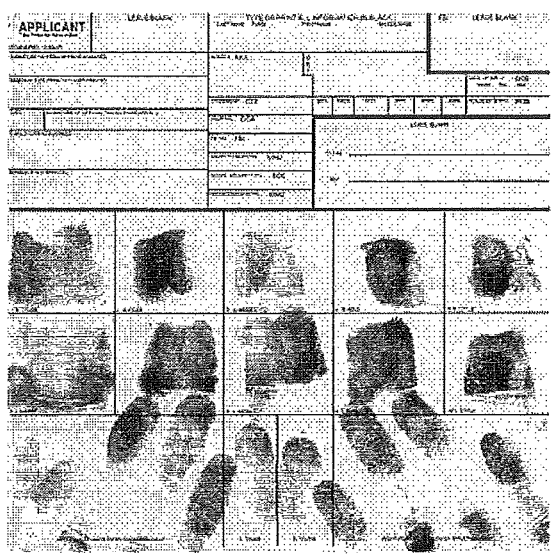
FIG. 4 is a view showing an example of a tenprint card.
Figure 5A:
FIG. 5A is a view showing a rolled print of a right index finger imprinted on a tenprint card image.
Figure 5B:
FIG. 5B is a view showing a slap print of the right index finger imprinted on the tenprint card image.

The image inputting device 10 inputs image data of a tenprint image as a grayscale image into the data processing device 20. The fingerprint image data is digital data. The image inputting device 10 scans a tenprint card to create the tenprint card image data. Or, the image inputting device 10 reads the tenprint card image data stored in a recording medium such as a magnetic disk or an optical disk. At this time, the data storing section 22 stores the tenprint card image data. FIG. 4 shows an example of the tenprint card image. The tenprint card image in FIG. 4 has fourteen ruled line frames for fingerprint images, and ten rolled prints and ten slap prints are imprinted. FIG. 5A shows a rolled print of the right index finger imprinted on the tenprint card image of FIG. 4. FIG. 5B shows a slap print of the right index finger imprinted on the tenprint card image of FIG. 4. Below, the case that the tenprint card input method is applied to the fingerprint image shown in FIG. 4 will be described.

(2) Step S2

Figure 6:
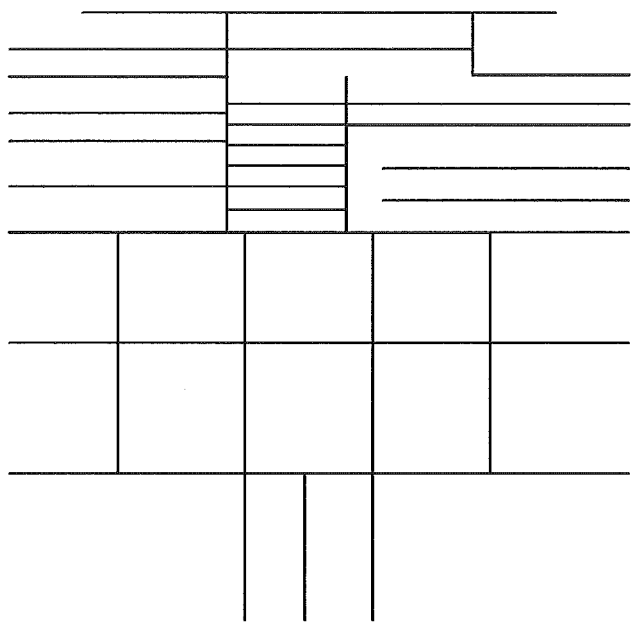
FIG. 6 is a view showing ruled line frames extracted from the tenprint card.
Figure 7:
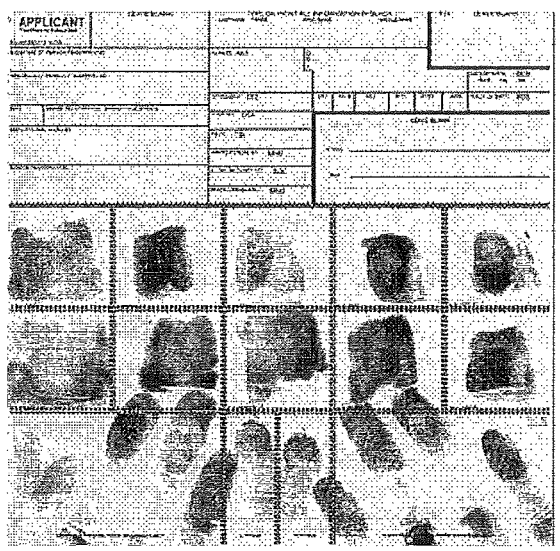
FIG. 7 is a view showing an example of a ruled line frame superimposed display on the tenprint card image.

The frame ruled line extracting section 23 analyzes the tenprint card image stored in the data storing section 22 and extracts the ruled line frames for the fourteen images. The extraction of the ruled lines can be easily realized by using a conventional technique. For example, it is possible to calculate density accumulation values in a horizontal direction and a vertical direction and detect peaks of the accumulation values. FIG. 6 shows the ruled line frames extracted from the tenprint card of FIG. 4. In addition, the ruled lines corresponding to the ruled line frames for the fourteen images where the fingerprints are imprinted can be easily assessed by analyzing a size and positional relationship of the ruled line frames. FIG. 7 shows an example that the detected ruled line frames for the fourteen images are superimposed onto the tenprint card image.

(3) Step S3

Figure 8A:
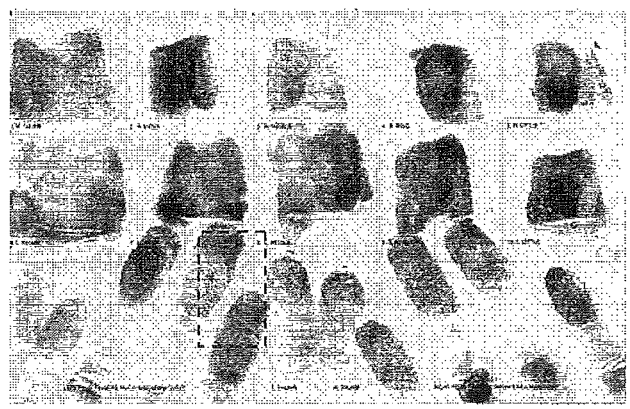
FIG. 8A is a view showing an example of fourteen images of the tenprint card after removing ruled line noise.
Figure 8B:
FIG. 8B is a view showing an example of an enlarged display of an image of a small region surrounded by a broken line before ruled lines are removed.
Figure 8C:
FIG. 8C is a view showing an example of an enlarged display of the image of the small region surrounded by the broken line after the ruled lines are removed.

The frame ruled line removing section 24 removes the ruled line frames for the fourteen images. This removal of the ruled lines can be realized by a conventional technique shown in the patent literature 4. FIG. 8A shows a fingerprint image region of the tenprint card where the ruled lines are removed as described above. FIG. 8B shows an enlarged display of an image of a small region surrounded by a broken line in FIG. 8A before the ruled lines are removed. FIG. 8C shows an enlarged display of the image of the small region surrounded by the broken line in FIG. 8A. That is, FIG. 8B shows the small region before the ruled lines are removed and FIG. 8C shows the small region after the ruled lines are removed. When FIG. 8C is compared with FIG. 8B, it is found that the ruled lines are effectively removed and the fingerprint ridges become clear in FIG. 8C.

(4) Step S4

Figure 9:
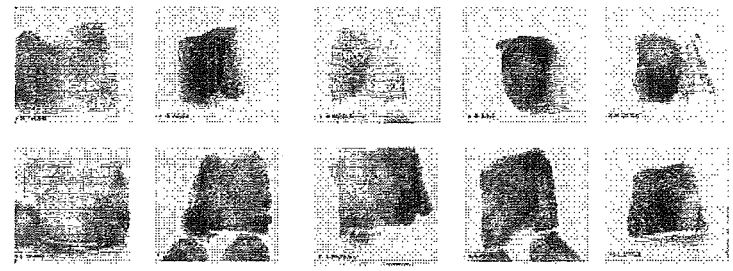
FIG. 9 is a view showing an example of images of rolled prints of ten fingers segmented for matching search.

The rolled print segmenting section 25 segments the rolled prints of ten fingers. A method of segmenting a rolled print for matching search according to the present invention is a simple method of clipping the rolled print along the ruled line frame corresponding to each finger. This rolled print is used for a search side in matching with respect to a slap print. FIG. 9 shows images of the rolled prints of ten fingers segmented for matching search.

(5) Step S5

Figure 10A:
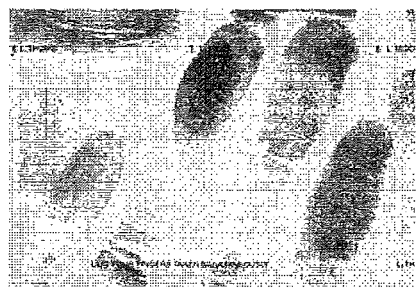
FIG. 10A is a view showing an example of an image of slap prints of four fingers of a left hand segmented for matching search.
Figure 10B:
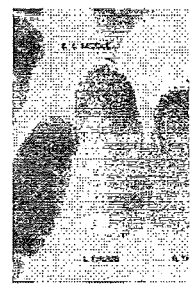
FIG. 10B is a view showing an example of an image of a slap print of a thumb finger of the left hand segmented for matching search.
Figure 10C:
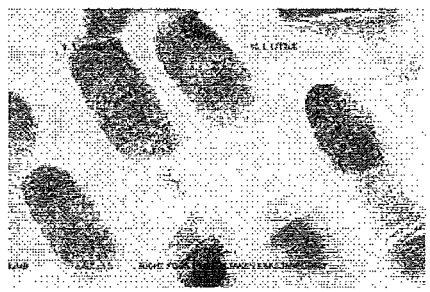
FIG. 10C is a view showing an example of an image of slap prints of four fingers of a right hand segmented for matching search.
Figure 10D:
FIG. 10D is a view showing an example of an image of a slap print of a thumb finger of the right hand segmented for matching search.
Figure 10E:
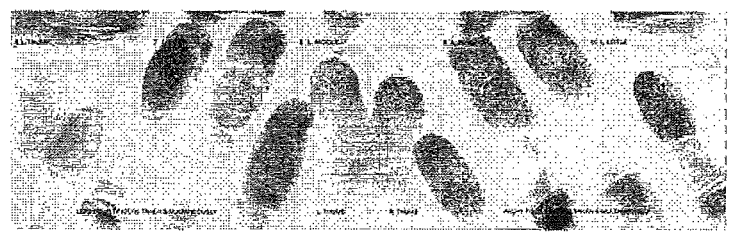
FIG. 10E is a view showing an example of an image of slap prints of ten fingers segmented for matching search.

The slap print segmenting section 26 segments the slap prints of four images used for matching objects. In the segmentation of slap prints used for matching objects, the slap print is segmented greater than the ruled line frame (here, extended beyond the frame by 0.4 inches or 200 pixels) and a portion protruded from (extended beyond) the frame is also contained in the slap print. FIGS. 10A to 10D show the slap prints of four images for matching objects segmented as described above. As shown in these figures, it is found that, since the slap print is segmented greater than the ruled line frame, the fingerprint region protruded from the frame is also contained in the slap print. In addition, instead of segmenting the slap prints of four images, for example, as shown in FIG. 10E, a whole image of slap prints of ten fingers may be used for slap prints for matching objects. However, in this case, it takes long time for matching as compared with matching using four regions, which is a weak point. Or, it may be considered that individual finger images are segmented from the image of the four-finger slap. However, in this case, if the segmentation of the individual fingers from the four-finger slap goes wrong, the expected matching result cannot be obtained, which is a weak point.

(6) Step S6

Figure 11A:
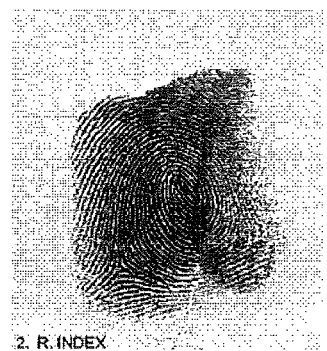
FIG. 11A is a view showing an example of an image of a rolled print of a right index finger for matching search.
Figure 11B:
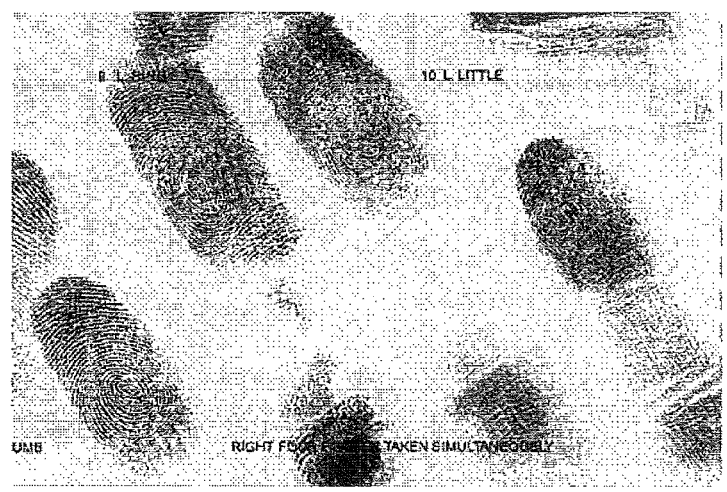
FIG. 11B is a view showing an example of an image of slap prints of four fingers of the right hand for matching search.

The fingerprint matching section 27 individually matches the segmented rolled print images of ten fingers for searching against the slap print images for matching objects in which respective fingers are contained. Here, by using feature point matching of a conventional technique shown in the non-patent literature 2 (JP 2003-173445A), the fingerprint matching is performed. When finding regions similar to each other as a result of the matching, the fingerprint matching section 27 outputs corresponding point information together with a matching score. Here, the corresponding point is a feature point pair judged that a feature point of the search side and a feature point of the matching object side correspond to each other. For example, when the rolled print image of the right index finger shown in the example of FIG. 11A is used for the searching side, the fingerprint matching section 27 matches it against the right four-finger slap image for matching objects shown in FIG. 10C. As a result, it is expected that a feature point is found on the slap print image of the right index finger. Here, FIG. 11B is an enlarged image of FIG. 10C.

(7) Step S7

Figure 12A:
FIG. 12A is a view showing an example of an image of a rolled print (search side) of a right index finger for matching search.
Figure 12B:
FIG. 12B is a view showing an example of an image of a slap print (matching object side) of a right index finger for matching search.

The corresponding common region extracting section 28 extracts a corresponding common region by using the corresponding point information as the matching result of the step S6. The corresponding common region is determined as regions neighboring the corresponding points and a region surrounded by the corresponding points. Or, a conventional technique disclosed in the patent literature 3 (JP 2004-078434A) may be used. FIG. 12A shows the rolled print for the searching and FIG. 12B shows the slap print corresponding to FIG. 12A which comes out from the result of the matching. This slap print is rotated such that its fingertip direction coincides with the fingertip direction of the rolled print of FIG. 12A. At this time, the corresponding common region extracting section 28 may rotate the slap print so as to adjust its fingertip direction to the fingertip direction of the rolled print of FIG. 12A as the slap print shown in FIG. 12B. FIGS. 12A and 12B show the corresponding common regions of two images as regions with diagonal lines surrounded by broken lines. These corresponding common regions are extracted by using a conventional technique as shown in the patent literature 3 (JP 2004-078434A).

(8) Step S8

Figure 12C:
FIG. 12C is a view showing an example of an image of a fingerprint region of a slap print of aright index finger.

The slap print segmenting section 26 determines slap print regions for outputting and segments slap prints of ten fingers for outputting. The slap print region for outputting is determined by extending the corresponding common region extracted at the step S7. However, in some cases, the extended region is connected to a fingerprint region of another finger. Therefore, when extending the corresponding common region, the slap print segmenting section 26 compares the extended region with fingerprint ridges inside the corresponding common region, and limits the extended region to a region where ridges are smoothly connected, that is, where continuity is high. In addition, the slap print segmenting section 26 removes a corresponding common region of another finger which comes out based on the matching of a rolled print of the other finger. FIG. 12C shows the fingerprint region of the slap print of the right index finger, which is determined as described above. As shown in FIG. 12C, the fingerprint region is segmented containing the ridge region protruded from the ruled line frame.

By repeating the processings of the steps S4 to S8 for the rolled prints of ten fingers for searching, the segmentation regions of the rolled print regions of ten fingers can be determined.

(9) Step S9

Figure 13:
FIG. 13 is a view showing an example of an image of a rolled print (a rolled print for outputting) of a left ring finger in which a part of a region of a slap print is removed.
Figure 14:
FIG. 14 is a view showing an example of images of rolled prints of ten fingers and slap prints of ten fingers for outputting.

The rolled print segmenting section 25 segments rolled prints of ten fingers for outputting. This processing can be achieved by removing the image region of the slap print segmented at the step S8 from the image of the rolled print for searching segmented at the step S4. For example, when a fingertip region of a slap print of a right ring finger is imprinted in a frame of a rolled print of a left ring finger, if this region can be judged as a part of the slap print, this region is removed from the rolled fingerprint image. FIG. 13 shows the rolled print of the left ring finger in which a part of the region of the slap print is removed as described above. FIG. 14 shows the rolled prints of ten fingers and the slap prints often fingers segmented by the above-described sequence of the processings. It is found that the slap prints are segmented containing the regions protruded from the frames.

(10) Step S10

The corresponding relationship checking section 29 checks a corresponding relationship between the rolled prints for outputting and the slap prints for outputting and detects an error of imprinting position. In addition, the corresponding relationship checking section 29 assesses the finger positions and detects an error of imprinting finger position. If the corresponding relationship has inconsistency, there is possibility that the imprinting position is wrong, and thus the corresponding relationship checking section 29 outputs a warning message indicating that fact. The detail of the corresponding relationship check will be described later.

(11) Step S11

The data processing controlling section 21 extracts the rolled prints of ten fingers and the slap prints of ten fingers segmented by the above-described processings and the check result at the step S10 from the data storing section 22. Then, the data processing controlling section 21 outputs them through the image outputting section 13 to the outside and finishes the sequence of the processings.

[Corresponding Relationship Check]

Next, the detail of the corresponding relationship check at the step S10 will be described.

For example, in the case of a right thumb finger, when a right thumb finger rolled print is matched against a right thumb finger slap print image for a matching object, if a corresponding common region is found (a corresponding common region is extracted), it is judged that imprinting positions of both of the rolled print and the slap print are correct. If a corresponding common region is not found (a corresponding common region is not extracted) against the right thumb finger slap print image, it is presumed that an imprinting position of any of the rolled print and the slap print is wrong. Therefore, a warning message indicating that fact is outputted to prompt an operator to check.

Before this warning message is outputted, it is considered that matching is performed against a corresponding slap print image of an opposite side hand (a reversed hand) as another implementation idea. When the reversed hand is used (in this case, when the right thumb finger rolled print is matched against a left thumb finger slap print image for a matching object), if a corresponding common region is found, a warning message indicating that fact is outputted. Consequently, the check of an operator can be easier.

In addition, for example, in the case of a right index finger to a right little finger, when respective rolled prints are matched against a right four-finger slap image for matching objects, if corresponding common regions are found and there is no inconsistency in a positional relationship of the corresponding common regions, it is judged that imprinting positions of both of the rolled prints and the slap prints are correct.

Usually, in the positional relationship of the four-finger slap in the right hand, a corresponding common region of an index finger, a corresponding common region of a middle finger, a corresponding common region of an ring finger and a corresponding common region of a little finger are arranged in this order from a left side. Therefore, if this relationship does not hold, it can be judged that there is inconsistency in the positional relationship.

If a corresponding common region is not found or there is inconsistency in the positional relationship of the corresponding common regions, it is presumed that imprinting positions of any of the rolled prints and the slap prints are wrong. Therefore, a warning message indicating that fact is outputted to prompt an operator to check.

When there is inconsistency in the positional relationship of the corresponding common regions, if the corresponding common region of at least one of four fingers is found, it is judged that the imprinting positions of the slap prints are correct and the imprinting positions of the rolled prints are wrong. However, if the corresponding common regions of whole four fingers are not found, there is a possibility that imprinting positions of the four-finger slap are wrong. For example, there is a possibility that the rolled prints and the slap prints are reversed hand.

Also, for the left five fingers, check as described above similar to that for the right five fingers is performed.

CONCLUSION

As described above, the present invention provides, in a tenprint card input processing, a method of segmenting fingerprint regions of respective fingers from the tenprint card, and a method of detecting an error of an imprinting position in high accuracy.

Specifically, the present invention provides, in a system executing computer-processing of a tenprint card where fingerprint images are imprinted, a processing mechanism for automatically segmenting the respective fingerprint images on the tenprint card.

Particularly, the present invention provides, even if a fingerprint image of a slap print does not fit into a predetermined frame or even if there is noise other than a fingerprint which is an object for segmentation inside a frame of a four-finger slap, a processing mechanism which can appropriately segment the slap print image by using a matching result against a rolled print.

In addition, the present invention provides a processing mechanism which checks a corresponding relationship between rolled prints and slap prints, detects an error of imprinting position, assesses finger positions and detects an error of imprinting finger position.

As a result, the appropriate fingerprint regions can be segmented, and the error of imprinting position and the error of imprinting finger position can be reduced. Thus, improvement of the accuracy of the fingerprint matching can be expected.

For example, when a tenprint card is inputted by using the conventional technique, usually, images are segmented and their digital images are created according to frames for fourteen images.

Figure 15:
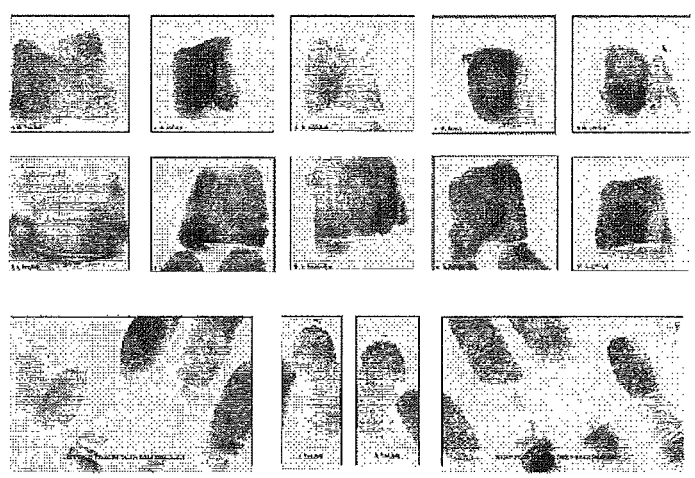
FIG. 15 is a view showing an example of fourteen images which are digital images created by a conventional technique.

FIG. 15 shows an example that the tenprint card of FIG. 4 is inputted by using the conventional technique and fourteen images are created as digital images.

There is a problem that, if a fingerprint is not imprinted appropriately inside the frame, a fingerprint region protruded from the frame is removed. Specifically, regarding a four-finger slap, there are many fingerprints protruded from the frame, the lack of the fingerprint regions is problem.

As shown in FIG. 15, it is found that, in the image of the four-finger slap, the fingerprint regions protruded from the frames are removed.

Moreover, there is a problem that individual fingerprints cannot be segmented from the four-finger slap image if the slap prints are not appropriately imprinted in the frame.

Even if the individual fingerprints can be segmented from the four-finger slap image, they are not perfect fingerprints. Therefore, there is a problem that matching against the rolled prints goes wrong, and consequently the check of the error of imprinting position goes wrong.

Figure 16:
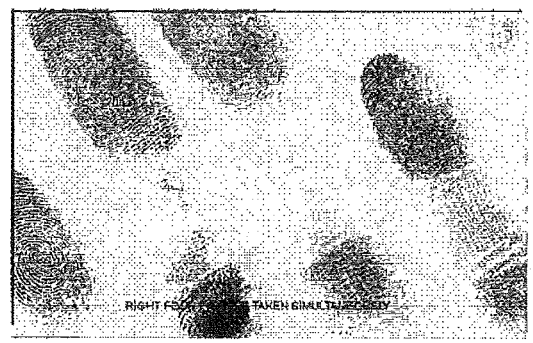
FIG. 16 is a view showing an example of images of individual fingerprints (there are fingerprint regions extended beyond the frame) which are segmented from a four-finger slap of a right hand.
Figure 16:
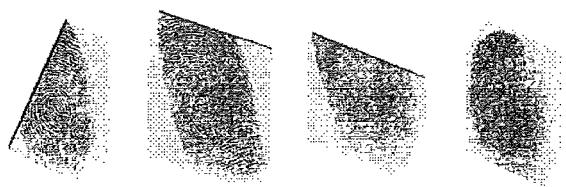

FIG. 16 shows an example that individual fingerprints are segmented from the right four-finger slap image. As shown in FIG. 16, it is found that the fingerprint regions protruded from the frame are lacked.

Furthermore, there is a problem that, if fingerprint impressions more than five fingers inside the frame of the four-finger slap or if there is noise on a paper base, four fingers cannot be segmented appropriately.

Figure 17:
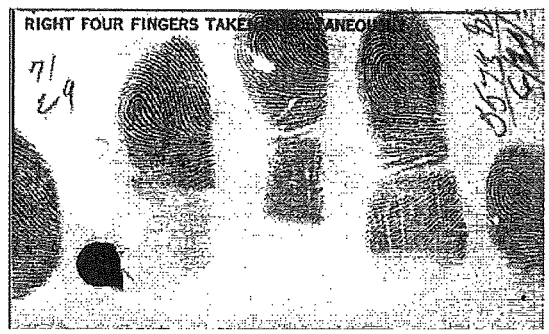
FIG. 17 is a view showing an example of images of fingerprint impressions of five fingers in a frame of a four-finger slap of a right hand.
Figure 17:
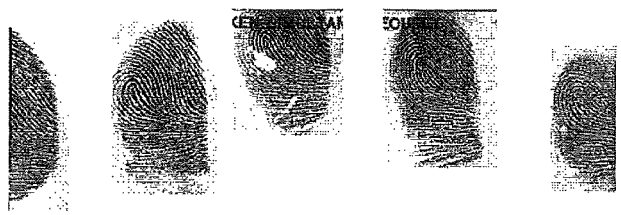

FIG. 17 shows an example of fingerprint impressions of five fingers inside the frame of the four-finger slap. In this case, four fingers cannot be segmented appropriately, and consequently the check of the error of imprinting position goes wrong.

Moreover, there is a problem that, even if the fingerprint can be segmented containing the region protruded from the frame by scanning the slap print largely beyond the frame ruled line, the ruled lines of the frame exists on the fingerprint ridges, and therefore, the matching accuracy is degraded.

In addition, an automatic processing technique that can appropriately segment the fingerprint image protruded from the frame is not established, an operator should manually specify the image, which makes operation burden heavy.

Accordingly, the present invention provides a processing mechanism which can appropriately segment the slap print image by using a matching result against the rolled print even if there is a fingerprint region protruded from a frame in slap images of ten fingers imprinted on the tenprint card or even if there is noise other than a fingerprint which is an object for segmentation inside a frame of a four-finger slap image. In addition, the present invention provides a processing mechanism which effectively removes the ruled lines of the frame. Furthermore, the present invention provides a processing mechanism which can improve the accuracy of the fingerprint segmentation even if quality of the four-finger slap image is low.

As a result, the appropriate segmentation of the fingerprint regions can be achieved, and the error of imprinting position can be reduced. Therefore, the accuracy of the fingerprint matching can be improved.

The whole or part of the exemplary embodiments disclosed above can be described as, but not limited to, the following supplementary notes.

(Supplementary Note 1)

A tenprint card input device includes:

a processing mechanism configured to segments a slap print image when a rolled print is segmented from a tenprint card as a searching side, the slap print image being that a slap print whose finger position is the same as the rolled print is imprinted, and the slap print image being segmented as a region externally greater than a ruled line frame by at least 0.4 inches;

a processing mechanism configured to perform fingerprint matching of the rolled print against the slap print as the slap print image as a matching object; and a processing mechanism configured to segment a region continuing a corresponding common region determined based on a result of the fingerprint matching as a region of the corresponding slap print.

(Supplementary Note 2)

The tenprint card input device according to the supplementary note 1, further includes:

a processing mechanism configured to appropriately segment the slap print image by matching the rolled print against the slap print even if there is noise other than a fingerprint which is an object for segmentation inside a frame of a four-finger slap image.

(Supplementary Note 3)

The tenprint card input device according to the supplementary note 1, further includes:

a processing mechanism configured to remove the ruled line frame.

(Supplementary Note 4)

The tenprint card input device according to the supplementary note 1, further includes:

a processing mechanism configured to rotate, by using a difference of a fingertip direction determined based on a result of the fingerprint matching between the rolled print and the slap print, the slap print image such that the fingertip direction coincides with that of the rolled print and output the slap print image.

<Remark>

While the invention has been particularly shown and described with reference to exemplary embodiments thereof, the invention is not limited to these exemplary embodiments. It is apparent that various changes in form and details may be made therein without departing from the spirit and scope of the present invention.

This application is based upon and claims the benefit of priority from Japanese patent application No. JP 2011-094029, the disclosure of which is incorporated herein in its entirety by reference.

What is claimed is:

1. A device, comprising:
a memory; and
a processor coupled to the memory,
wherein the processor performs operations, the operations comprising:
reading a tenprint card image which includes a plurality of fingerprint patterns and ruled lines being frames of a fingerprint imprint area and a next fingerprint imprint area;
segmenting a portion of the tenprint card image into a fingerprint image, the fingerprint image including straddling fingerprint patterns straddling between a part of the fingerprint imprint area and a part of the next fingerprint imprint area; and
outputting a digital image of the segmented fingerprint image including the straddling fingerprint patterns.

2. The device of claim 1, wherein the fingerprint image includes a slap fingerprint image, and
wherein the operations further comprise extracting from the tenprint card image a slap fingerprint image of which a slap fingerprint pattern lies across two fingerprint imprint areas.

3. The device of claim 1, the operations further comprising:
extracting from the tenprint card image at least two fingerprint images which include a same part of the fingerprint imprint area.

4. The device of claim 1, the operations further comprising detecting the ruled lines in the segmented fingerprint image; and removing the ruled lines overlapping the segmented fingerprint image.

5. The device of claim 1, the operations further comprising: detecting the ruled lines in the segmented fingerprint image.

6. The device of claim 1, the operations further comprising: removing the ruled lines overlapping the segmented fingerprint image.

7. The device of claim 6, wherein, in the removing the ruled lines, fingerprint ridges become clear.

8. The device of claim 6, wherein the removing the ruled lines includes processing the segmented fingerprint image such that fingerprint ridges become clear.

9. The device of claim 1, wherein the processor outputs the digital image of the segmented fingerprint image including the straddling fingerprint patterns to a display device.

10. The device of claim 1, wherein the processor outputs the digital image of the segmented fingerprint image including the straddling fingerprint patterns to one of a printer that prints contents of the digital image of the segmented fingerprint image including the straddling fingerprint patterns and a projector that projects the contents of the digital image of the segmented fingerprint image including the straddling fingerprint patterns.

11. A method, comprising:
reading a tenprint card image which includes a plurality of fingerprint patterns and ruled lines being frames of a fingerprint imprint area and a next fingerprint imprint area;
segmenting a portion of the tenprint card image into a fingerprint image, the fingerprint image including straddling fingerprint patterns straddling between a part of the fingerprint imprint area and a part of the next fingerprint imprint area; and
outputting a digital image of the segmented fingerprint image including the straddling fingerprint patterns.

12. The method of claim 11, wherein the fingerprint image includes a slap fingerprint image, and
wherein the method farther comprises extracting from the tenprint card image a slap fingerprint image of which a slap fingerprint pattern lies across two fingerprint imprint areas.

13. The method of claim 11, further comprising:
extracting from the tenprint card image at least two fingerprint images which include a same part of the fingerprint imprint area.

14. The method of claim 11, further comprising: detecting the ruled lines in the segmented fingerprint image; and removing the ruled lines overlapping the segmented fingerprint image.

15. The method of claim 11, further comprising: detecting the ruled lines in the segmented fingerprint image.

16. The method of claim 11, further comprising: removing the ruled lines overlapping the segmented fingerprint image.

17. The method of claim 11, wherein the outputting comprises sending the digital image of the segmented fingerprint image including the straddling fingerprint patterns to a display device.

18. The method of claim 11, wherein the outputting comprises sending the digital image of the segmented fingerprint image including the straddling fingerprint patterns to a printer to print contents of the digital image of the segmented fingerprint image including the straddling fingerprint patterns.

19. The method of claim 11, wherein the outputting comprises sending the digital image of the segmented fingerprint image including the straddling fingerprint patterns to a projector to project contents of the digital image of the segmented fingerprint image including the straddling fingerprint patterns.

* * * * *